United States Patent [19]

Healy

[11] Patent Number: 4,757,817
[45] Date of Patent: Jul. 19, 1988

[54] ADHESIVE ELECTRODE PAD
[75] Inventor: James W. Healy, Sagle, Id.
[73] Assignee: Lead-Lok, Inc., Sandpoint, Id.
[21] Appl. No.: 23,535
[22] Filed: Mar. 9, 1987
[51] Int. Cl.$^4$ .............................................. A61B 5/04
[52] U.S. Cl. ................................................... 128/641
[58] Field of Search .............................. 128/639–641, 128/644, 798, 802, 803

[56] References Cited

U.S. PATENT DOCUMENTS

| | | | |
|---|---|---|---|
| 3,805,769 | 4/1974 | Sessions | 128/641 |
| 4,270,544 | 6/1981 | Gilden et al. | 128/640 |
| 4,331,153 | 5/1982 | Healy | 128/641 |
| 4,649,923 | 3/1987 | Hoffman | 128/641 |

Primary Examiner—Lee S. Cohen
Attorney, Agent, or Firm—Wells, St. John & Roberts

[57] ABSTRACT

An electrode pad is provided with a cut to form a substantially rectangular tab that can be lifted out of the plane of the main pad portion. An aperture is included at the end of the cut to receive an electrical connector wire extending from a connector mounted to an electrode fitting on the pad. A carrier sheet is removably attached to an adhesive surface of the pad. The carrier is separated by the cut into two separable sections that can be removed separately from the pad to facilitate placement of the line and to minimize patient discomfort. By this arrangement, the carrier sheet can be removed and the main pad portion pressed against the patient's skin before the tab is lifted up. The tab section of the carrier sheet is then removed to expose the adhesive surface. The tab is then placed over the electrode line extending from the electrode fitting on the main portion to hold the line securely to the patient's skin adjacent to the main portion of the pad. Relative movement between the electrode connector and electrode fitting on the pad is thus inhibited and thereby artifacts are avoided.

7 Claims, 2 Drawing Sheets

U.S. Patent  Jul. 19, 1988  Sheet 1 of 2  4,757,817
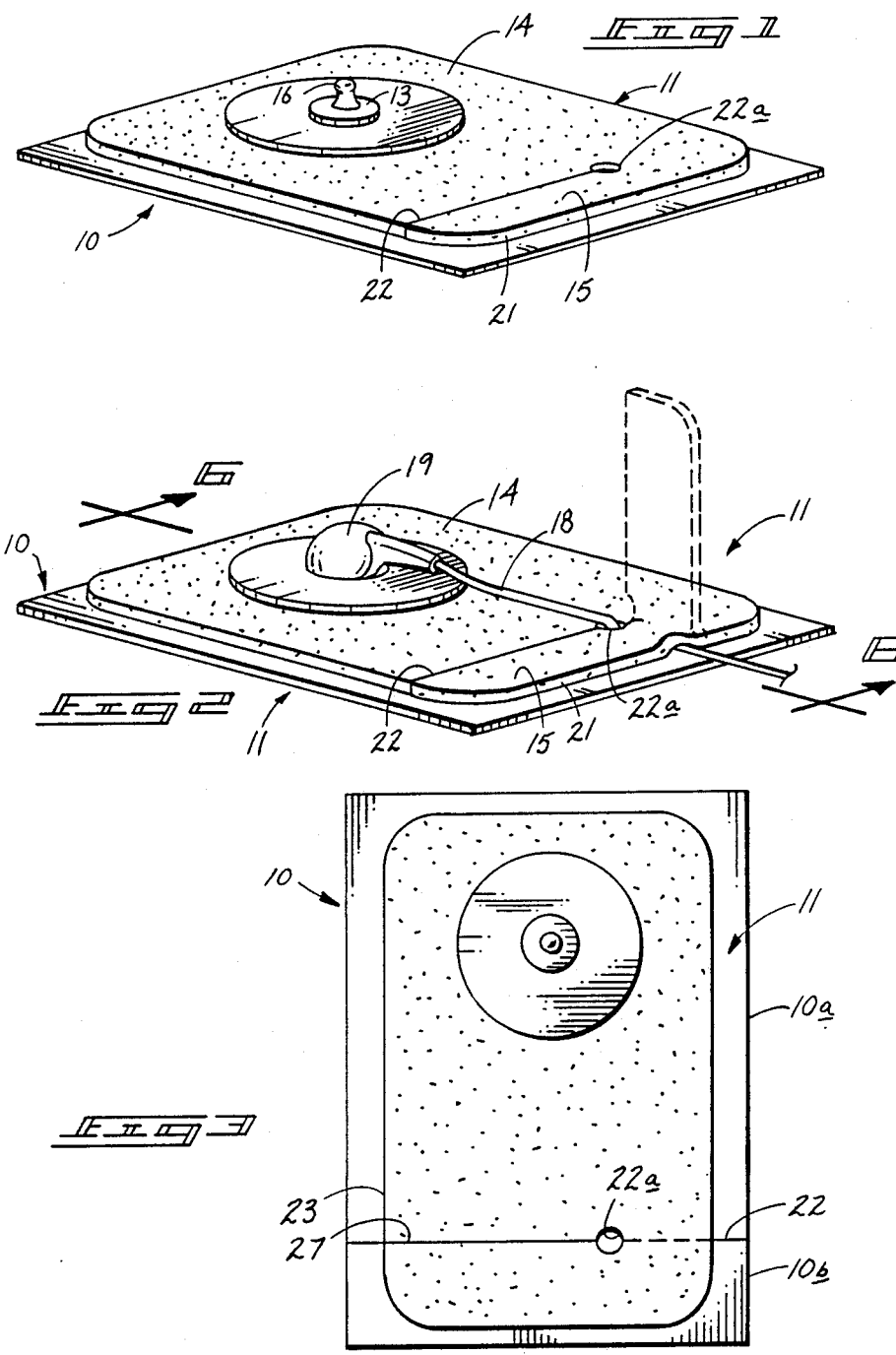

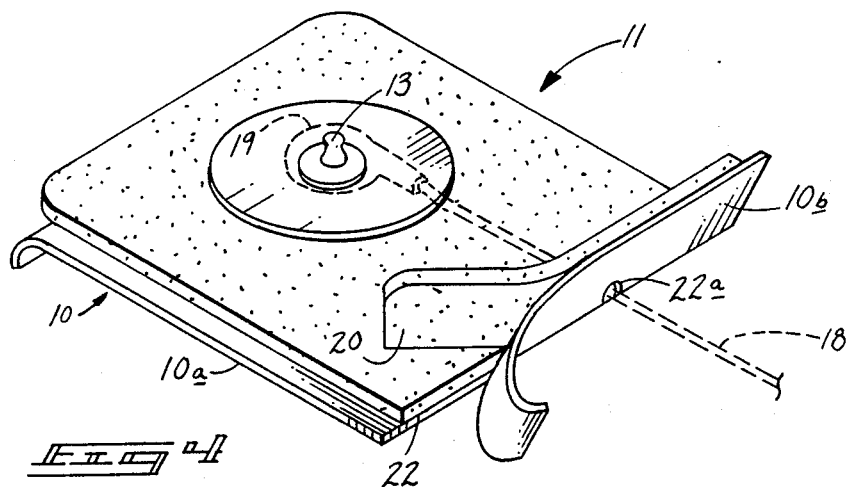
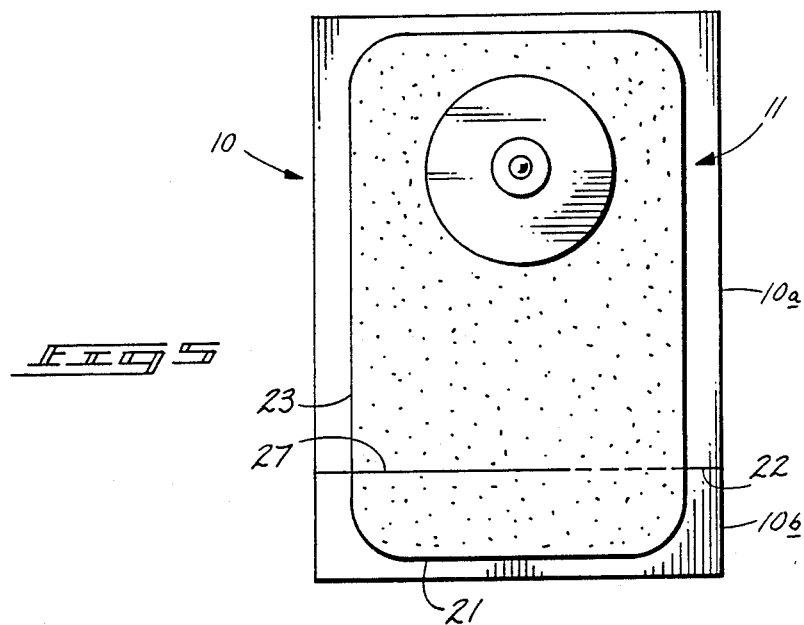
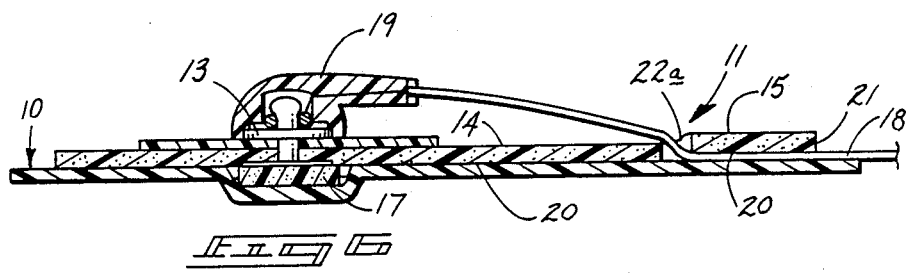

ADHESIVE ELECTRODE PAD

TECHNICAL FIELD

This invention relates to an improved adhesive electrode pad and particularly to such a pad that provides capabilites for securing an electrode line and connector to the pad.

BACKGROUND OF THE INVENTION

Most present day medical electrode pads are of the disposable type. The typical pad includes a pad member surrounding an electrode and includes an adhesive material on its bottom surface except for a central portion which contains a conductive jelly for making good electrical contact with a patient's skin when the pad is pressed in place. A cable terminating in an electrode connector is connected to an electrode projection on the pad so that proper electrical connection is effected. Several such disposable electrode pads may be located at strategic positions on a patient and small electrical signals indicative of the function being monitored may be recorded.

After the record has been completed, the electrode connectors are removed from the electrode projections on the electrode pad. The pad is then simply removed from the patient and thrown away.

Problems currently experienced with many present day electrodes may be summarized as follows:

1. Artifacts (spurious signals) are cuased by relative movement between the electrode and the electrode connector resulting from movement of the electrical connector line extending from the electrical connector. Such movement can be a result of the relatively long lines used in some instances as well as from the movements of the patient.

2. Artifacts are also generated when the impedance between the metallic electrode and the patient's skin changes. Such impedance change is caused by an increased space between the skin and the electrode when the connector line is pulling against the electrode.

3. Patient movements often cause the breakage of connector lines due to tension.

4. Because of the freedom of movement of the connector line, there is wear on the line and frequent replacement is often necessary.

The foregoing problems have plagued the hospital industry since the inception of disposable type electrodes. As an attempted solution, large quantities of adhesive tape have been used to tape the lines to the patient. For example, if portions of the line extending from the connector could be taped to the patient it is clear that relative movements between the connector and the electrode projection itself would be substantially reduced since movements of the remaining portions of the line beyond those portions fastened to the patient would have little effect on the connecting portions to the electrode. However, utilizing conventional adhesive tape in this manner has brought along many new problems. For example, the large quantity of adhesive tape for each of the electrodes involved (and there may be 4-6 electrodes during any one recording session) obstructs other diagnostic procedures including defibrillation. Further, the adhesive tape itself is irritating to the patient and requires shaving of a large skin area if it is to be effected in adhering to the skin. This latter problem creates another problem in the increased cost and time for skin preparation. Finally, there is general discomfort to the patient when the various cables or lead wires are mass-taped to his skin.

The above problems have been solved to a substantial degree by the pad disclosed in U.S. Pat. No. 4,331,153 granted to the present applicant in 1982. The disposable electrode disclosed therein includes a pad with a cut extending inward from one side to form an auxiliary pad portion. The auxiliary pad portion is used to secure the electrode line in relation to the patient's skin and to the electrode.

While the above device has met with commercial success as a practical product for securing the electrode line in place, several difficulties have been noted through its extensive use in the field. Firstly, the cut simply extends into the pad and terminates at a closed end with no clearance being provided for passage of the electrode line nor any visual indication as to where the line should be placed. As a result, it is not unusual for the auxiliary pad portion to be distorted upon placement of the line underneath. It has also been found that the auxiliary pad will sometimes tear as the auxiliary pad portion is lifted to receive a portion of the electrode line.

Another difficulty has been discovered during clinical application of the electrode pad and auxiliary pad portion to a patient. Previously, the entire pad, including the auxiliary pad portion, were supplied on plastic carrier sheets that serves as the removable adhesive backing for both sections of the pad. The pads would be removed entirely from the carrier sheet and attached to the patient. The auxiliary pad portion would also tend to adhesively attach to the patient at the time the main pad body would be attached. It would then be required that the auxiliary pad portion be detached from the patient to lift the auxiliary pad upwardly in order to receive the electrode line. This would cause discomfort to the patient by the detachment of the adhesive surface of the auxiliary pad portion from the skin tissues and would decrease the final effective holding power of the adhesive along this portion of the pad.

Another problem occurred with the shape of the auxiliary pad portions. The auxiliary pad portions were formed along arcuate edges of the pad and the cut was similary arcuate. The resulting configuration of the auxiliary pad portion was therefore a somewhat tapered triangular configuration. The triangular configuration did not always provide sufficient adhesive area to adequately secure the electrode line in a stationary relationship to the associated electrode. This was also due in part to the reduced holding capability as indicated above when the auxiliary pad portion was pulled from the patient's skin and then reapplied after the electrical line had been positioned.

BRIEF DESCRIPTION OF THE DRAWINGS

The present pad is illustrated in the accompanying drawings, in which:

FIG. 1 is a pictorial view of a first form of the present electrode pad;

FIG. 2 is a pictorial view similar to FIG. 1 only showing mounting of an electrode connector and line to the pad;

FIG. 3 is a top plan view of the present pad with a divided carrier sheet;

FIG. 4 is a pictorial view illustrating removal of the independent carrier sheet sections;

FIG. 5 is a top plan view of an embodiment similar to that shown in FIG. 3 without an aperture formed through the pad; and FIG. 6 is an enlarged sectional view taken substantially along line 6—6 in FIG. 2.

DETAILED DESCRIPTION OF THE PREFERRED EMBODIMENTS

The following disclosure of the invention is submitted in compliance with the constitutional purpose of the Patent Laws "to promote the progress of science and useful arts" (Article 1, Section 8).

In FIG. 1, there is shown a plastic carrier sheet 10 for supporting an electrode pad designated generally by the numeral 11. The arrangement is such that the electrode pad is readily manually accessible and can be successively peeled off from the plastic carrier sheet 10 when it is to be used. In fact several of the pads 11 may be supplied on a single carrier sheet 10.

The present pad 11 generally comprises a pad of pliable material including a main body portion 14 and a tab 15. An electrode 13 including an electrical fitting 16 is carried on the substantially flat top surface of the main portion 14 while a conductive jelly 17 is carried on the bottom surface of the main portion. The conductive jelly is in electrically conductive relationship through the main portion 14 of the pad with the electrode 13.

The electrode 13 cooperates with an electrical connector line 18 extending from an appropriate recording device (not shownn) and terminating in an electrode connector 19 arranged to be received over the electrical fitting 16 to thereby connect the line 18 to the conductive jelly and thus to the patient's skin when the pad 13 is pressed to the patient's skin.

In order to secure the pad to a specific area of the patient's skin, the area in question is normally shaved clean of hair and the pad is then firmly pressed into place on the shaved area. The adhesive surface shown at 20 preferably covers the remaining portion of the bottom surface of the pad not covered by the conductive jelly 17.

The tab 15 is defined between one edge 21 of the pad and a cut 22 formed in the pad extending from an adjacent edge 23 towards an opposite edge and terminating short of the opposite edge. The arrangement is such that the tab 15 can then be lifted out of the plane of the main portion 14 of the pad as shown in FIG. 2 by dashed lines.

The cut 22 is advantageously straight and parallel to one side edge 21 of the pad to form the tab in a substantially rectangular configuration. The tab thus formed includes a maximum surface area of contact for the portion of adhesive surface 20 that extends along the bottom side of the tab 15. The adhesive surface of the tab is thereby afforded a maximum grip on an engaged portion of the electrical line and the patient's skin to hold the line 18 between the gripped portion and electrode connector 19 stationary relative to the electrode 13.

The first preferred form of the cut 22 extends to an inward end where an aperture 22a extends through the pad. The aperture 22a is provided to receive the electrical connector line in such a manner that the tab 15 will not tear or become distorted.

The aperture 22a may be substantially cylindrical with a diameter larger than the cross-sectional dimension of the connector line 18 to clearly identify the preferred location for passage of the line and so the line will be freely received therein. The aperture 22a also functions to reduce the danger of the tab 15 being torn off the pad as the tab is lifted relative to the main pad portion 14 to receive the line.

In the embodiment shown in FIGS. 1, 2 and 6, the carrier sheet 10 is solid so the entire pad is removed from the sheet prior to application to the patient's skin. Placement of the electrode connector 19 and line 18 on the pad is advantageously accomplished before application of the pad to the patient. This is done by lifting the tab 15 on the carrier sheet, attaching the connector 19 to the fitting 16 and passing the line through the aperture 22a. The tab can then be folded back slightly to secure the adhesive surface 20 to the line seciton now spanning the bottom side of the tab 15. The entire pad may then be removed from the carrier sheet and be pressed to the patient's skin, with the tab also being pressed flat against the skin surface to secure the line and connector in place.

In the embodiments illustrated in FIGS. 3–5 the carrier sheet 10 is separated as the cut 22 exends part way through the pad and fully across the width of the sheet 10. The cut 22 thus separates the sheet 10 into two sections, a main body section 10a releasably covering the bottom adhesive surface 20 adjacent the electrode 13, and a tab section 10b releasably covering the bottom adhesive surface of the tab 15. The two sheet sections 10a, 10b can be removed from the pad independently of one another. This is advantageous both to the attendant and to the patient. The separate tab sheet section 10b can be lifted along with the tab 15 to the tab position shown dashed line in FIG. 2 by the attendant for placement of the line 18. The line can then be fitted through the cut 22 in the FIG. 5 embodiment, or the opening 22a in the FIG. 3 embodiment without exposing the adhesive surface. The covered tab 15 will not stick to the attendant's fingers during this step and the adhesive will remain fresh since it has not previously been attached to the patient's skin. The tab sheet section 10b can thus remain in place on the tab 15 until after the adhesive surface of the main section has been attached to the patient and the line is in place. This saves the patient the discomfort of having the tab pulled away from the skin to receive the line 18.

The embodiment shown in FIG. 3 includes a combination of the advantageous features of the separable carrier sheet sections 10a and 10b and the cut with aperture 22a. With this arrangement, the first sheet section 10a may be removed and bottom surface of the main portion 14 of the pad can be pressed against a patient's skin as described so that the conductive jelly will bear against the skin in conductive relationship. The connector, if not mounted earlier, can now be attahced to the fitting. The tab 15 is then lifted up as shown in FIG. 2 and the line is moved into the aperture 22a. The tab section 10b of the carrier sheet can then be removed so the tab 15 can be pressed down against the patient's skin. The portion of the line held under the pad is adjacent to the electrode connector and thus will serve to hold the connector essentially immobile relative to the electrode fitting.

It can be appreciated that if the line 18 were not taped down by the tab 15, rotation, tilting, upward and downward translation movements of the connector 19 relative to the electrode could result in spurious signals produced through the electrode not only from changes in contact pressure but also from changes in impedance between the conductive jelly and the skin particularly when the electrode is subject to tension along the line to pull the electrode away from the skin.

By providing the tab in the manner described, by means of a cut formed into a side of the pad, ending at the aperture 22a and by provision of the separate tab carrier sheet section 10b, the tab is conveniently available for immediate use in receiving and taping down the line portion extending from the connector 19.

From all the foregoing, it will now be evident that the present invention has provided in a very simple manner an improved electrode pad which exhibits a surprising and remarkable number of advantages in that various problems heretofore involved are overcome. The solution proposed by my present invention is not only extremely simple but inexpensive and does not require any appreciable changes in manufacturing technique.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

I claim:

1. In an adhesive electrode pad including a relatively flat pad body having a top surface, an opposite adhesive bottom surface and an electrode with an electrical fitting on the top surface for releasable attachment to an electrical connector on an electrical connector line, the invention characterized by:
   a cut formed in the pad body extending from a peripheral edge of the pad to an inward end, thereby forming a tab with a portion of the adhesive surface on a tab bottom surface, the tab being angularly foldable in relation to the top surface of the pad body;
   the cut including an aperture formed through the pad at the inward cut end;
   wherein the aperture is of sufficient size to freely receive the electrical connector line thereby avoiding distortion of the tab when the tab is pressed over the electrical connector line to secure the electrical connector against undesired movement relative to the electrode.

2. In an adhesive electrode pad as claimed by claim 1 further characterized in that the aperture is substantially cylindrical and of a diameter adapted to be slightly greater than the cross-sectional dimension of the electrical connector line.

3. In an adhesive electrode pad wherein the pad includes a substantially straight side edge as claimed by claim 1 and further characterized in that the cut is substantially straight and parallel to the pad side edge thereby forming the tab in a substantially rectangular configuration to maximize surface contact area of the portion of adhesive surface on the tab bottom surface.

4. In an adhesive electrode pad including a relatively flat pad body having a top surface, an opposite adhesive bottom surface a carrier sheet removably connected to the adhesive bottom surface, and an electrode with an electrical fitting on the top surface for releasable attachment to an electrical connector on an electrical connector line, the invention characterized by:
   a cut formed in the pad body extending from a peripheral edge of the pad to an inward end, thereby forming a tab including a portion of the adhesive bottom surface that can be lifted angularly in relation to the top surface of the pad body to receive a portion of the connector line along the tab portion of the adhesive bottom surface;
   wherein the cut extends through the carrier sheet to separate the carrier sheet into a main body section releasably contacting the adhesive surface on the pad body adjacent the electrode and a tab section releasably contacting the adhesive bottom surface of the tab, the main body section and tab section being individually separable from the adhesive bottom surface so the electrode pad can be secured to a selected surface sequentially by first removing the main body section of the carrier sheet and pressing the exposed adhesive to the selected surface and subsequently removing the tab section of the carrier sheet and pressing the exposed adhesive bottom surface of the tab to the selected surface and over a portion of the electrical line adjacent the electrical connector to secure the electrical connector against undesired motion relative to the electrode.

5. In an adhesive electrode pad including a relatively flat pad body having a top surface, an opposite adhesive bottom surface, a carrier sheet removably connected to the adhesive bottom surface and a substantially centrally located electrode with an electrical fitting on the top surface for releasable attachment to an electrical connector on an electrical connector line, the invention characterized by:
   a cut formed in the pad body extending from a peripheral edge of the pad to an inward end, thereby forming a tab including a portion of the adhesive bottom surface that can be lifted angularly in relation to the top surface of the pad body;
   the cut including an aperture formed through the pad at the inward cut end;
   wherein the cut extends through the carrier sheet to separate the carrier sheet into a body section releasably contacting the adhesive surface on the pad body adjacent the electrode and a tab section releasably contacting the adhesive bottom surface of the tab, the sections being individually separable from the adhesive bottom surface so the electrode pad can be secured to a selected surface sequentially by first removing the body section of the carrier sheet and pressing the exposed adhesive to the selected surface and subsequently removing the tab section of the carrier sheet and pressing the exposed adhesive bottom surface of the tab to the selected surface and over a portion of the electrical line adjacent the electrical connector to secure the elecrical connector against undesired motion relative to the electrode; and
   wherein the aperture is of sufficient size to freely receive the electrical connector line thereby avoiding distortion of the tab when the tab is pressed over the electrical connector line to secure the line adjacent the electrical connector relative to the electrode.

6. In an adhesive electrode pad as claimed by claim 5 further characterized in that the aperture is substantially cylindrical and of a diameter adapted to be slightly greater than the cross-sectional dimension of the electrical connector line.

7. In an adhesive electrode pad including a relatively straight side edge as claimed by claim 5 and further characterized in that the cut is substantially straight and parallel to the pad side edge thereby forming the tab in a substantially rectangular configuration to maximize surface contact area of the portion of adhesive surface on the tab bottom surface.

* * * * *